US005662699A

United States Patent [19]
Hamedi et al.

[11] Patent Number: 5,662,699
[45] Date of Patent: Sep. 2, 1997

[54] METHOD AND APPARATUS FOR STIMULATING OR MONITORING THE EXERCISE OF MUSCLES ADJACENT A BODY CAVITY

[75] Inventors: Hassan Hamedi, Milwaukee; H. Wilfred Lynch, New Glarus; Vaughan B. Weeks, Racine, all of Wis.

[73] Assignee: Myo Kinetic Systems, Inc., Menomonee Falls, Wis.

[21] Appl. No.: 525,330

[22] Filed: Sep. 8, 1995

Related U.S. Application Data

[63] Continuation-in-part of Ser. No. 168,705, Dec. 16, 1993, abandoned.

[51] Int. Cl.$^6$ ......................................... A61N 1/04
[52] U.S. Cl. .................... 607/138; 607/40; 607/41; 128/761; 128/778
[58] Field of Search ........................ 128/733, 761, 128/778; 607/40, 41, 133, 138

[56] References Cited

U.S. PATENT DOCUMENTS

| | | | |
|---|---|---|---|
| 3,866,613 | 2/1975 | Kenny et al. | 128/408 |
| 4,106,511 | 8/1978 | Erlandsson | 128/407 |
| 4,216,783 | 8/1980 | Kaiser et al. | 128/778 |
| 4,296,760 | 10/1981 | Carlsson et al. | 128/788 |
| 4,396,019 | 8/1983 | Perry, Jr. | 128/733 |
| 4,564,024 | 1/1986 | Woller, Jr. | 607/133 |
| 4,653,514 | 3/1987 | Shapiro | 128/778 |
| 4,768,522 | 9/1988 | Shapiro | 128/778 |
| 4,881,526 | 11/1989 | Johnson et al. | 128/24.5 |
| 5,010,895 | 4/1991 | Maurer et al. | 128/788 |
| 5,199,443 | 4/1993 | Maurer et al. | 128/788 |

FOREIGN PATENT DOCUMENTS

| | | | |
|---|---|---|---|
| 2547203 | 12/1984 | France | 607/138 |
| 197712 | 12/1977 | U.S.S.R. | 607/138 |
| 9324176 | 12/1993 | WIPO | 607/41 |

OTHER PUBLICATIONS

A 1992 brochure published by Empi, Inc. entitled INNOVA Feminine Incontinence Treatment Design Rationale.
An undated specification sheet published by Compass Medical Technologies, Inc. illustrating and describing 7 vaginal/rectal probes, admitted prior art.
Fall, Does Electrostimulation Cure Urinary Incontinence?, 131 The Journal of Urology 664–667 (1984).
Eriksen and Eik-Nes Long-Term of the Pelvic Floor: Primary Therapy in Female Stress Incontinency?, 44 Urology International 90–95 (1989).
An undated brochure published by Empi, Inc. entitled Intravaginal Stimulation for Urinary Incontinence and containing abstracts of ten articles.

*Primary Examiner*—Lee S. Cohen
*Assistant Examiner*—Stephen Huang
*Attorney, Agent, or Firm*—Miller, Simon, McGinn & Clark S.C.

[57] ABSTRACT

Methods, and apparatus used in the methods, for stimulating, and monitoring the exercise of, muscles near a body cavity by transmitting electrical energy between an electrical source or processor and the wall of the body cavity. A flexible airtight sheath with a resilient skeleton and outer conductive bands is collapsed by vacuum and inserted into the body cavity. Air is allowed to enter so that the skeleton expands the sheath and forces the conductive bands against the body cavity wall. The skeleton may be a foam member, internal ribs or a separate internal frame. The leads for conducting electrical energy to and from the bands may be embedded in the bands for a substantial portion of the band circumference, or the leads may be connected to the bands by piercing conductive mounds on the bands or by being joined to conductive straps on the bands.

14 Claims, 8 Drawing Sheets

METHOD AND APPARATUS FOR STIMULATING OR MONITORING THE EXERCISE OF MUSCLES ADJACENT A BODY CAVITY

This is a continuation-in-part of application Ser. No. 08/168,705, now abandoned, filed Dec. 16, 1993.

FIELD OF THE INVENTION

The invention relates to methods and apparatus for electrically stimulating muscles near a body cavity and for monitoring electrical signals generated by the exercise of such muscles for biofeedback purposes.

BACKGROUND

It is known to treat female urinary incontinence with electrical stimulation applied to the walls of the vagina via electrodes carried by a probe inserted into the vagina. See, for example, Eriksen and Eik-Ness, Long-Term Electrostimulation of the Pelvic Floor: Primary Therapy in Female Stress Incontinence, 44 Urology International 90–95 (1989); Fall, Does Electrostimulation Cure Urinary Incontinence?, 131 The Journal of Urology 664–667 (1984). By activating pudendal nerve branches, such stimulation causes contraction of the muscles of the pelvic floor. Repeated sessions of such stimulation can strengthen and retrain those muscles and thereby alleviate stress incontinence in which urine passes with the onset of abdominal pressure which may result from stressed or quick activities, including sneezing and jumping. Repeated sessions of such electrical stimulation can also alleviate urge incontinence, which results from involuntary bladder contractions; the electrical stimulation apparently inhibits reflex actions of the various pelvic nerves which are responsible for bladder control.

An electrode-carrying insert has also been used in electromyographical biofeedback treatments. In those usages, the electrodes on the insert transmit electrical signals in the other direction—i.e., the electrodes detect from the vaginal or rectal wall the minute electrical impulses resulting from muscle activity and transmit those impulses to electrical components which display them to the patient. The patient utilizes the display in a biofeedback process to develop conscious and willful control over his or her muscles. U.S. Pat. No. 4,396,019, Perry, Jr., Aug. 2, 1983.

One type of intravaginal electrode-carrying insert is relatively rigid. It will accommodate electrodes in the form of bands around the insert, which optimizes the effectiveness of the insert in delivering the signals to the vagina wall. See e.g., U.S. Pat. No. 4,881,526. With this type of insert, it is typically the practice to provide a wide variety of sizes in order to be able to fit each individual patient. Even if a proper fit is initially made, it may cease to fit well because of changes in the size of the woman's vagina which can result from changes in body position and hormone levels. In these cases, and even in well-fit cases, maintaining the insert in proper position for effective transmission of electrical stimulation to the targeted portions of the vaginal wall has been a problem. A further problem of the rigid insert is that insertion can be difficult since the insert is rigid and must be large enough to effectively contact the body cavity walls.

The ideal electrode-carrying body cavity insert would (a) fit body cavities of different sizes, (b) be easily inserted, (c) remain at the desired location in the body cavity, (d) provide good electrical contact with the body cavity walls and (e) be easily removed. The last two decades have seen numerous efforts to meet this ideal:

| Date* | Country | Doc # | Inventor | Insert Feature |
|---|---|---|---|---|
| 1974 | U.S. | 3,866,613 | Kenny | Adjustable ring |
| 1976 | U.S. | 4,106,511 | Erlandsson | Inflate inside cavity |
| 1978 | U.S. | 4,296,760 | Carlsson | Inflate inside cavity |
| 1983 | FR | 2,547,203 | Pigne | Foam provides structure |
| 1989 | U.S. | 5,010,895 | Maurer | Rolled-up sheet |
| 1992 | WO | 93/24176 | Tippey | Inflate inside cavity |
|  |  |  | Tippey | Foam provides structure |

*The date is the priority date.

This effort was not entirely successful. Mechanically adjustable inserts, such as the adjustable ring and the rolled-up sheet, can be inconvenient and uncomfortable to use and may not make full and consistent contact with the walls of the body cavity. The inflate-inside inserts can be relatively convenient to insert and remove, but require the maintenance of air pressure during the entire period of use (which requires greater manufacturing expense to prevent leakage), and when rigid enough to make effective electrical contact, they may be too rigid to adapt to the exact shape and size of the particular body cavity, resulting in partial and inconsistent contact with the walls of the body cavity. The foam-filled inserts do not require the maintenance of air pressure during use and can adapt to the cavity, but they are more difficult to insert and remove since it is in its expanded state during insertion and removal.

Parallel with this effort, in 1984 (U.S. filing date) there was developed a non-electric vaginal insert to enhance the effectiveness of Kegel-type vaginal exercises. U.S. Pat. No. 4,653,514 (Shapiro, Mar. 31, 1987). The electrode was filled with a foam to provide resistive force to the vaginal walls, against which a women could exert her pelvic muscles and thereby strengthen them. To provide beneficial exercise, the foam had to be relatively stiff. To facilitate insertion and removal of an insert filled with such foam, the insert was provided with a pump to evacuate the air from, and thereby collapse, the insert. When the insert was in place, the vacuum was released and the foam expanded to the vaginal walls and thereby held the insert in place without the need to maintain air pressure during use.

The foregoing chronology shows that, five years after the publication of the Shapiro patent, persons skilled in the electrode-insert art (such as Tippey, et. al) continued along the well trod path, developing an improved inflate-inside electrode-insert and an improved foam-filled electrode-insert. There remained a need for an electrode-insert which overcomes the disadvantages of these devices.

SUMMARY OF THE INVENTION

The objects of the invention are to meet that need.

The invention provides methods for (a) stimulating muscles near a body cavity and (b) monitoring the electrical energy generated by the exercise of muscles near a body cavity wall, by transmitting electrical energy between an electrical source or processor and the wall of the body cavity. Both methods include the step of providing a substantially airtight sheath having a resilient skeleton which in the absence of opposing forces provides the sheath with a shape and size such that the sheath yieldingly impinges on the body cavity wall when the sheath is installed in the body cavity. The sheath has at least a pair of electrically conductive portions insulated from each other and an aperture between the exterior and the interior of the sheath. A second common step is providing a pump and placing it removably in communication through the aperture with air in the sheath such that operating the pump evacuates air from the sheath and thereby collapses the insert. Further common steps are collapsing the insert by operating the pump, removing the pump and closing the aperture, inserting the insert into the body cavity, opening the aperture to allow air to return into the sheath so that the resilient skeleton expands the insert and the conductive portions yieldingly and conductively engage the body cavity wall. The conductive portions are electrically connected to an electrical source (stimulation method) or and electrical processor (exercise monitoring method). In the stimulation method, the electrical source is operated so that electrical energy flows from it through one conductive portion to the cavity wall and thence into the other conductive portion and back to the electrical source. In the exercise monitoring method, the user exercises muscles near the body cavity so that muscle-activity electrical energy flows from the body cavity wall to the processor. Additional common steps are electrically disconnecting the electrical source or processor from the conductive portions, placing the pump in communication with the aperture, operating the pump to collapse the insert, and removing the insert.

In another aspect, the invention provides a body cavity insert for transmitting electrical energy between the body cavity wall and an electrical device. There is provided a substantially airtight, flexible sheath which has at least a pair of flexible, electrically-conductive portions insulated from each other. The sheath has a port for allowing air to flow into and out of the sheath. Within the sheath there is a resilient skeleton adapted to form and hold the sheath yieldingly against the body cavity wall when the insert is installed in the body cavity, in the absence of an opposing force. An electrical lead is connected to each of the electrically-conductive portions of the sheath, and the leads are disposed for a connection to an electrical device. A pump in communication with air in the sheath allows air to be evacuated from the sheath in order to collapse the insert for ease of insertion and removal. There is a substantially airtight barrier for closing the port to retain the insert in its collapsed state and for opening the port to allow air to return to the sheath so that the insert will expand until the conductive portions of the sheath yieldingly engage the body cavity wall.

In one preferred aspect, the conductive portions are bands which extend at least substantially around the sheath, and the leads are conductively embedded in the conductive bands for at least a substantial portion of the circumference of the bands around the sheath. The leads may be embedded by being sandwiched between two conductive layers. Alternatively, the leads may be stuck into a conductive mound form on the conductive band and may be further secured by adhesive or looping back and being fastened to a portion of the lead adjacent its point of entry into the mound. In another aspect, leads may be joined to a conductive strap formed on the conductive portion.

One advantage of the invention is that it facilitates easy insertion and removal but does not require the maintenance of internal air pressure during use. Another advantage is a reduction in the number of sizes which must be manufactured. A further advantage is that flexible electrodes will be yieldingly but relatively forcefully engaged against the body cavity wall, thereby enhancing electrical conduction and insert stability.

Other objects and advantages of the invention will be apparent from the description which follows.

BRIEF DESCRIPTION OF THE DRAWINGS

FIGS. 11a and 11b illustrate the sandwiched embedding of electrical leads in the electrodes;

DETAILED DESCRIPTION OF THE PREFERRED EMBODIMENTS

Although the invention is generally described herein in terms of an intravaginal embodiment for treating urinary incontinence in women, it is not limited to that. For example, it may be employed intravaginally to treat other conditions in which electrical transmission to or from a body cavity may be found beneficial. It may also be found useful to be employed intraanally in men or women to treat incontinence or other conditions.

Figures 1, 2:
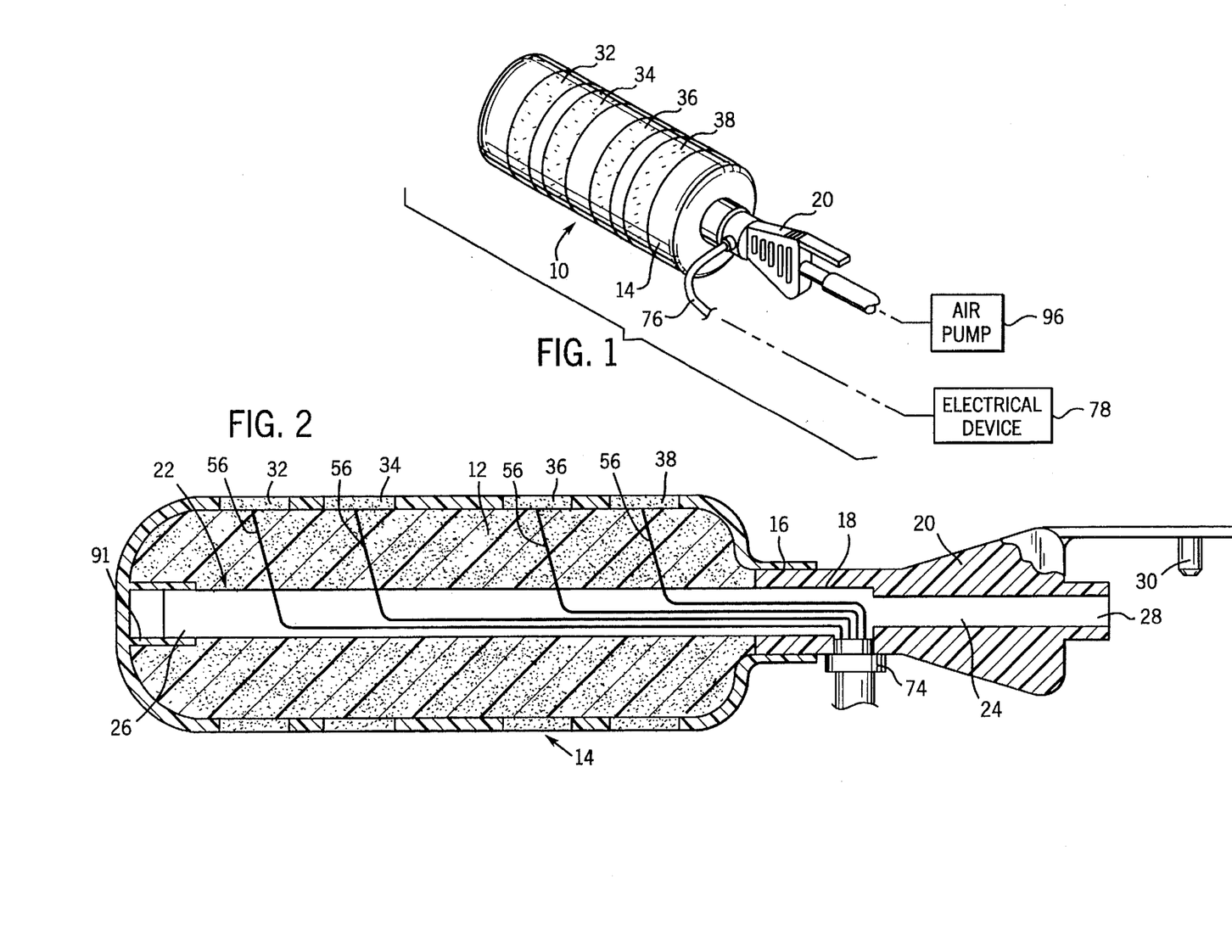
FIG. 1 is a perspective view of an intravaginal embodiment of the present invention.
FIGS. 2, 3 and 4 are cross-sectional, partially schematic views of three foam-filled embodiments of the present invention.
Figure 3:
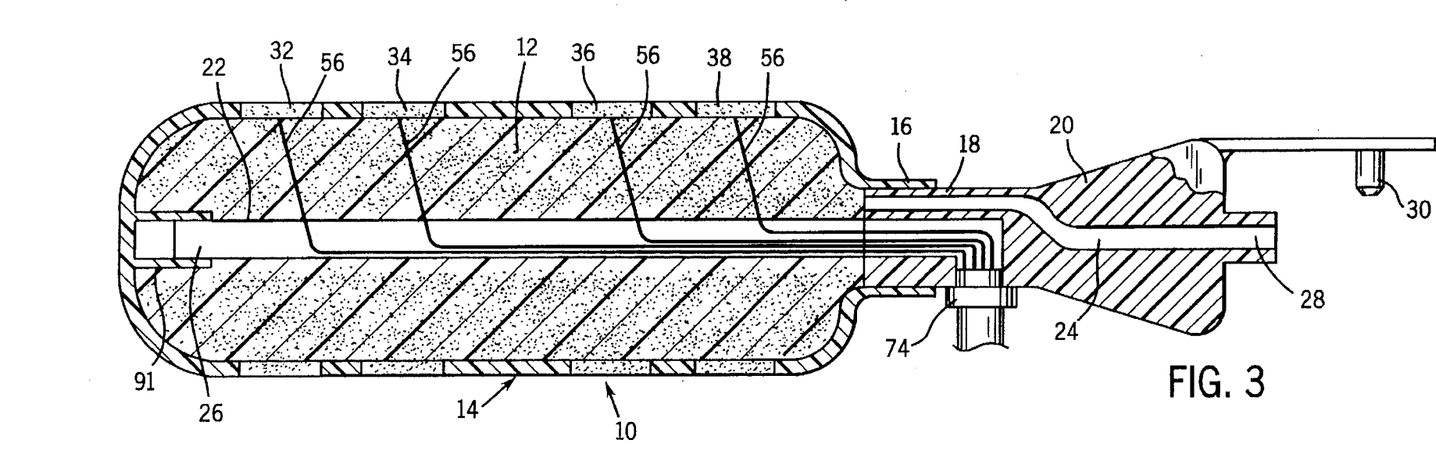

In the embodiment illustrated in FIGS. 1–3, vaginal insert 10 comprises a resilient filler member 12 having sponge-like resiliency characteristics. It is formed in a cylindrical shape and is covered by a substantially airtight sheath 14. The filler member 12 serves as a skeleton which can give the sheath 14 shape and structure. The sheath 14 is closed around the resilient filler member 12 except for an open collar 16 which is airtightly affixed to the neck 18 of a handle 20. The collar 16 serves, inter alia, as a port to allow air to flow into and out of the sheath 14. The handle 20 is affixed to or formed integrally with an elongated semi-rigid core 22 which extends longitudinally through the resilient filler member 12 and within the sheath 14.

Figure 4:
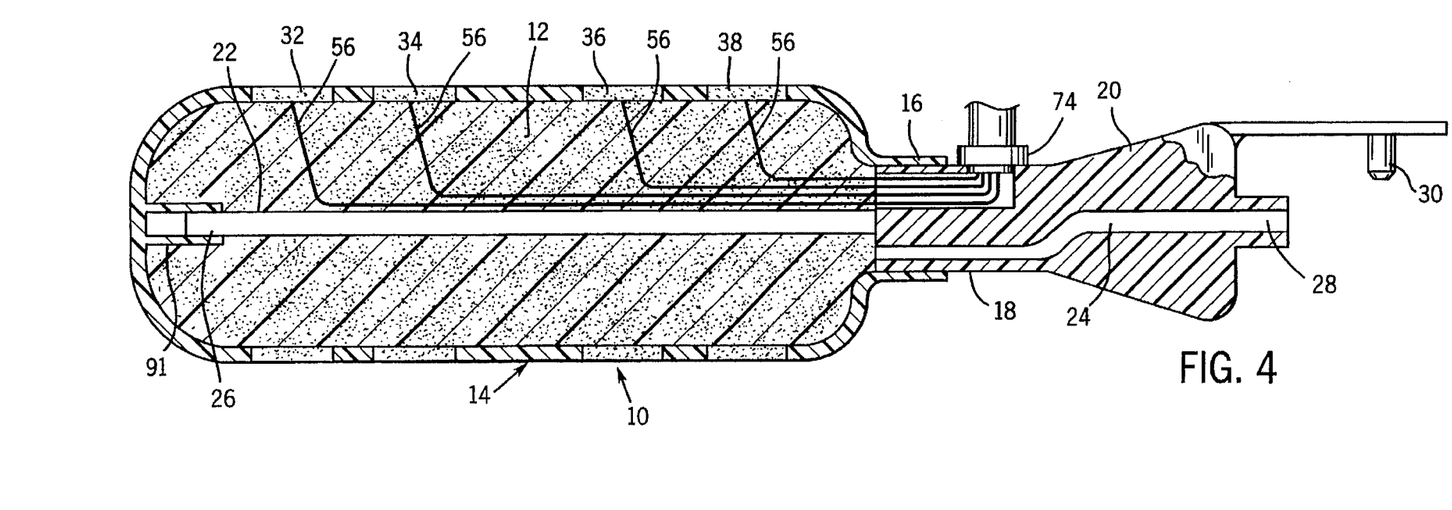
Figure 5:
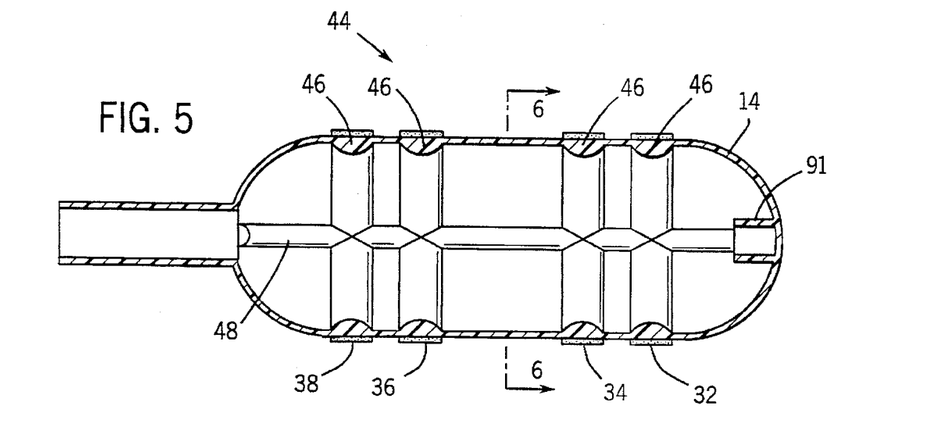
FIGS. 5 and 6 are longitudinal and lateral cross-sectional views respectively of an internally-ribbed embodiment of the present invention.
Figure 7:
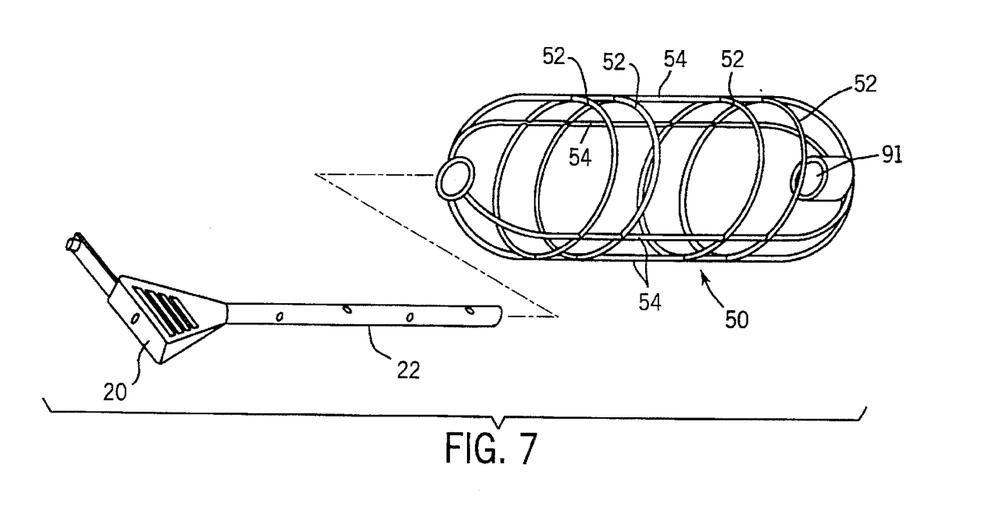
FIGS. 7–10 are a perspective view, an end view and lateral and longitudinal cross-sectional views of an internal frame for use in another embodiment of the claimed invention.
Figure 8:
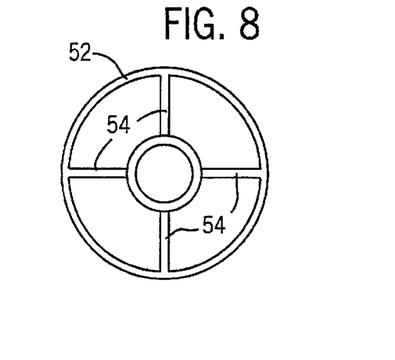
Figure 8B:
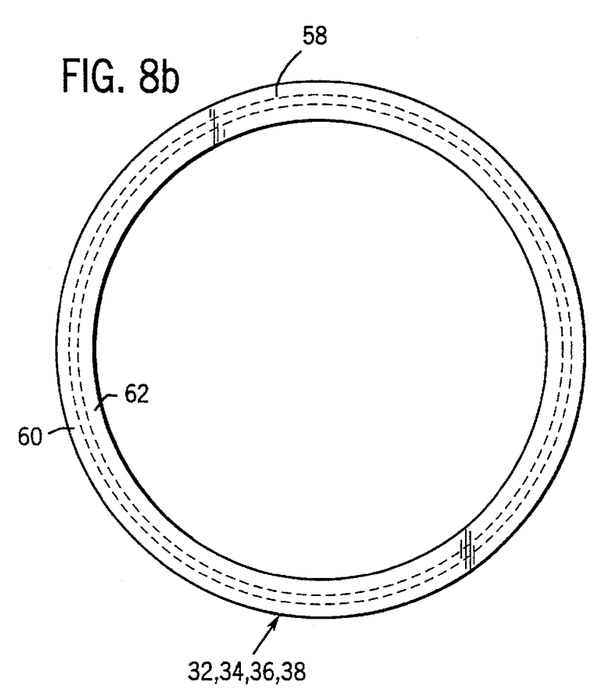
Figure 9:
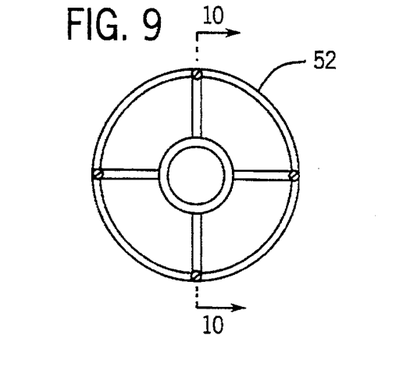
Figure 10:
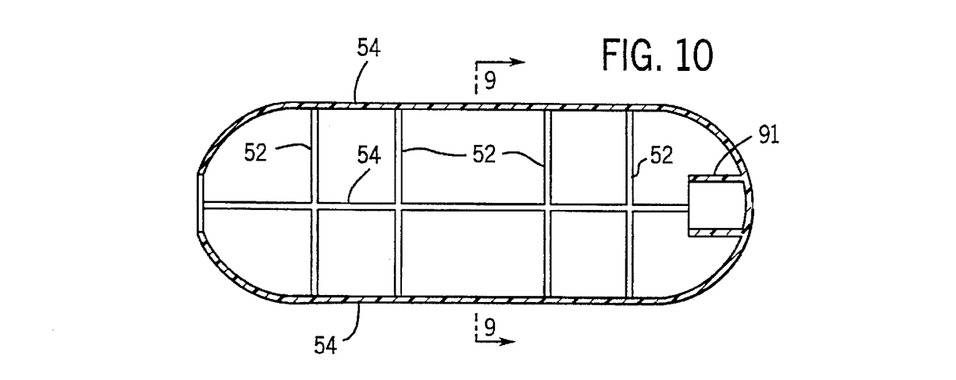

The handle 20 is provided with an air passageway 24 which communicates with the atmosphere and with the interior of the insert 10. The air passageway 24 may open directly into the resilient filler member 12 as is shown in FIGS. 3 and 4 or may communicate with an air passageway 26 in the core 22 (FIGS. 2 and 5). In the latter case, one or more holes are provided in core 22, at its end or along its length, to allow the passageway 26 to communicate with the interior of the insert 10. See, for example, FIG. 7. The outlet 28 of the handle air passageway 24 can be closed off by the insertion of a plug 30.

The sheath 14 includes four electrically-conductive portions, electrodes 32, 34, 36, 38. In the embodiments illustrated in the drawings, each of the electrodes 32, 34, 36, 38 is a band which encircles insert 10, although the invention is not so limited. The other portions of sheath 14 are not electrically-conductive and therefore insulate electrodes 32, 34, 36, 38 from each other.

Figures 16, 17, 18:
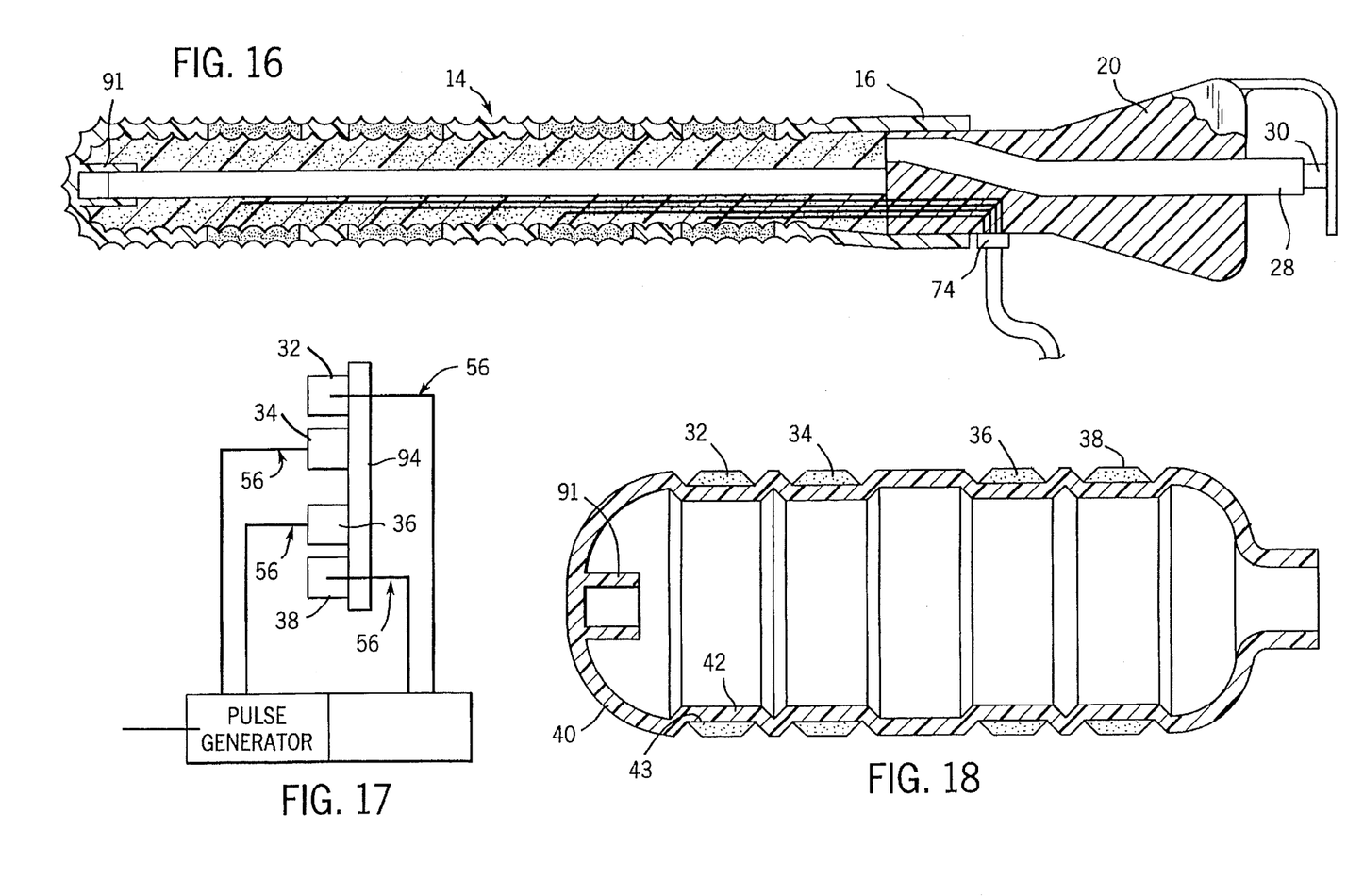
FIG. 16 illustrates the embodiment of FIGS. 2 & 3 in a collapsed state for insertion into the vagina.
FIG. 17 is a schematic representation of the electrical circuits formed when the insert is operating as an electro-therapy device.
FIG. 18 is a schematic representation of another embodiment of the insert.

The electrode bands may be molded separately from the non-conductive portions and joined to them in the course of making the sheath 14. FIG. 2 illustrates a sheath made in that way. Alternatively, the electrode bands 32, 34, 36, 38 may be adhesively attached to an all-non-conductive sheath base 40, as is illustrated in FIG. 18. The non-conductive base 40 is made with four wide annular grooves 42 onto which the electrode bands 32, 34, 36, 38 are joined with adhesive at the junction 43 between the groove 42 and the electrode bands 32, 34, 36, 38.

Figure 6:
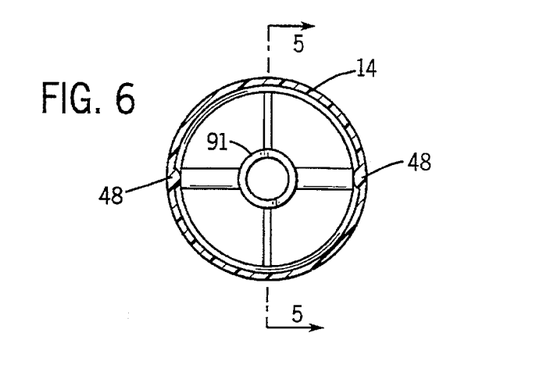

The embodiment 44 illustrated in FIGS. 5 and 6 is essentially the same as that of FIGS. 1–3 except that its skeleton is provided by inwardly thickened sections or ribs formed on the inner surface of the sheath 14 rather than by a foam resilient filler member. In the embodiment 44 illustrated in FIGS. 5 and 6, there are four laterally circumferential ribs 46, each one being located beneath one of the electrode bands 32, 34, 36, 38, and two longitudinal ribs 48. Locating the circumferential ribs 46 beneath the electrode bands enhances the electrical and mechanical contact between the electrode bands and the body cavity wall. There may, however, be more or fewer ribs than shown in FIGS. 5 and 6. The ribs need not be continuous. Breaks or cross section changes in the ribs may be employed to control both the force with which the ribs attempt to expand and the collapsed shape of the ribs.

These ribs 46, 48 can be produced in any of several ways. In one method, the mandrel which forms the inner cavity of the sheath 14 includes undercuts which form the ribs 46, 48 as the sheath 14 is molded. For this method it is preferable that the sheath material have an elongation at failure of greater than 300%, of which silicone rubber is an example. Another method is to form the rib portions in advance and place them in the mold for the sheath 14. When the sheath 14 was molded, the ribs would be insert molded into it. This method would allow the ribs to be of a different material from that of the sheath 14 or have different material properties than those of the sheath 14.

A relatively stiff elastomer is preferable for the ribs. Examples include silicone rubber and styrene-butadiene-styrene, of which an example is Kraton™, a product of Shell Oil Company, 1 Shell Plaza, P.O. Box 2463, Houston Tex. 77252. Another potential material is a silicone modified polymer such as C-Flex™ made by the Concept Company, Clearwater, Fla.

FIGS. 7–10 illustrate a component 50 of an embodiment which is similar to the embodiment of FIGS. 5 & 6 in not employing a foam resilient filler member but which uses an internal, but separate, resilient frame 50 as the skeleton to provide the shape and structure of the insert 10 when it is not collapsed. FIGS. 7–10 show such a frame 50. The frame 50 is made of a resilient material, such as silicone, which yields enough to be collapsed by a vacuum but which has enough stiffness when the vacuum is released to resume its normal state and press the insert 10 against the cavity wall with enough force to provide sufficient electrical and mechanical contact. In the embodiment of FIGS. 7–10, the frame 50 comprises four laterally circumferential members 52 and four longitudinal members 54, but there could be a different number of such members. Placing the circumferential members 52 beneath the electrode bands offers the advantages described above.

The frame 50 may be made of silicone or a thermoplastic elastomer such as Hytrel™ made by DuPont. If silicone is used, the frame 50 can be formed by transfer, compression or liquid injection molding. If thermoplastic elastomer is used, the frame 50 can be injection molded or formed from a stock of standard cross section (such as tubing) and ultrasonically or thermally welded. To facilitate insertion of the frame 50 into the sheath 14, the frame 50 could be collapsed or the sheath 14 expanded (such as by air pressure) or both.

Figure 11A:
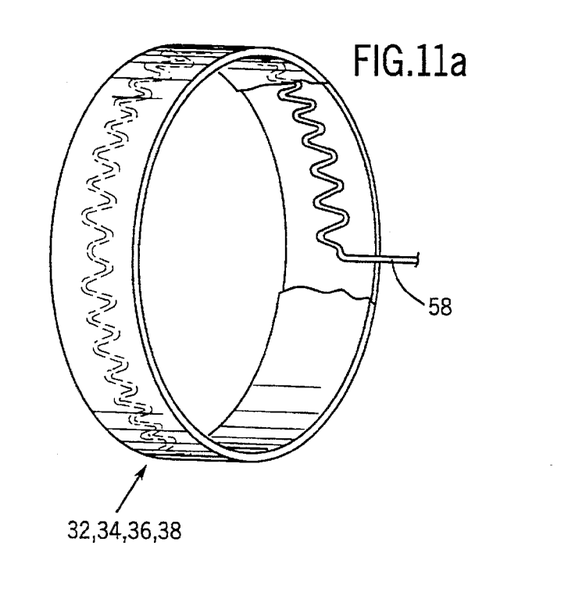

An electrical lead 56 is connected to each of the electrodes 32, 34, 36, 38. In one aspect of the invention, the connection is made during the manufacture of the electrodes by sandwiching a flexible wire 58 between two conductive layers 60, 62 of an electrode, as shown in FIGS. 11a and 11b. For example, the electrode may be made of a thermosetting material and the lead 56 may be placed between two layers 60, 62 which have a clay-like consistency before heating. In a further aspect of the invention, the flexible wire 58 which is sandwiched between layers 60 and 62 is given a zigzag shape (as shown in FIG. 11a) to reduce the risk of tearing the sheath 14 or breaking the flexible wire 58 despite repeated expansions and contractions of insert 10, and to enhance the electrical connection between the lead 56 and the layers 60, 62. As shown in FIG. 11a, the sandwiched flexible wire 58 can extend substantially all the way around the electrode. Connecting lead 56 to flexible wire 58, such as by soldering, can be facilitated by turning sheath 14 inside out before making the connection and then turning it right side in.

An electrical lead 56 can be connected to each of the electrodes 32, 34, 36 or 38 by other means as well. For example, the conductivity of electrodes 32, 34, 36 or 38 may be enhanced sufficiently, by additional carbon, copper or silver or by other means, to eliminate the need or desirability of embedding a wire 41 in these electrodes. In such a case, a one-point connection of a lead 56 to an electrode can be sufficient to allow efficient electrical conduction generally over the whole surface of the electrode.

Figure 12A:
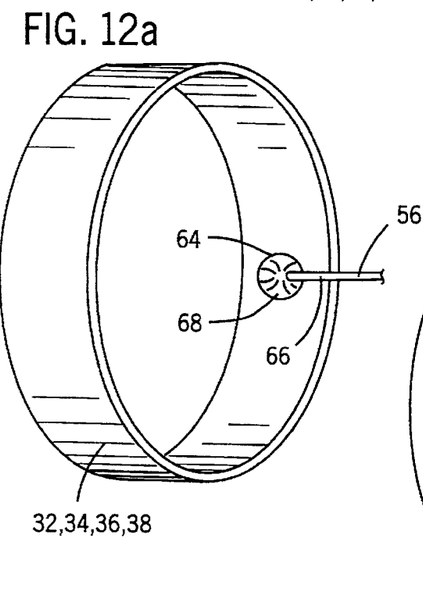
FIGS. 12a through 12d illustrate other structures for connecting an electrical lead to the electrodes.

In one aspect, this connection can be accomplished by molding a mound 64 (as shown in FIG. 12a) of conductive material on the inner surface of an electrode 32, 34, 36 or 38. An end 66 of lead 56, as if a needle, pierces and enters the mound 64, which exerts some resistance force tending to retain the lead 56 within it. This resistance force is supplemented by placing an adhesive on and around the junction 68 of the lead 56 and the mound 64.

Figure 12B:
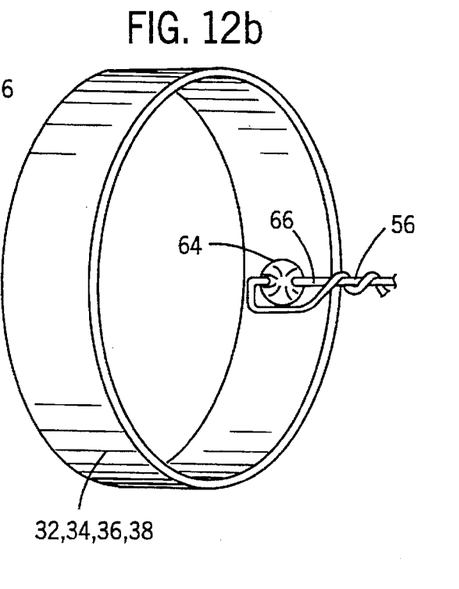

Alternatively, as shown in FIG. 12b, the end 66 is threaded through mound 64, looped back and joined (by a knot, wrapping, soldering, adhesive and/or other means) to lead 56 near the junction 68 of the lead 56 and mound 64.

Figure 12C:
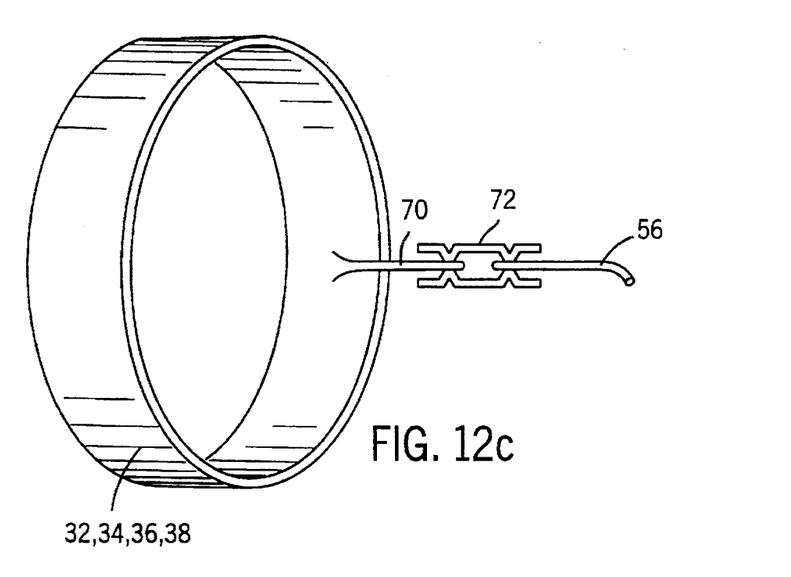
Figure 12D:
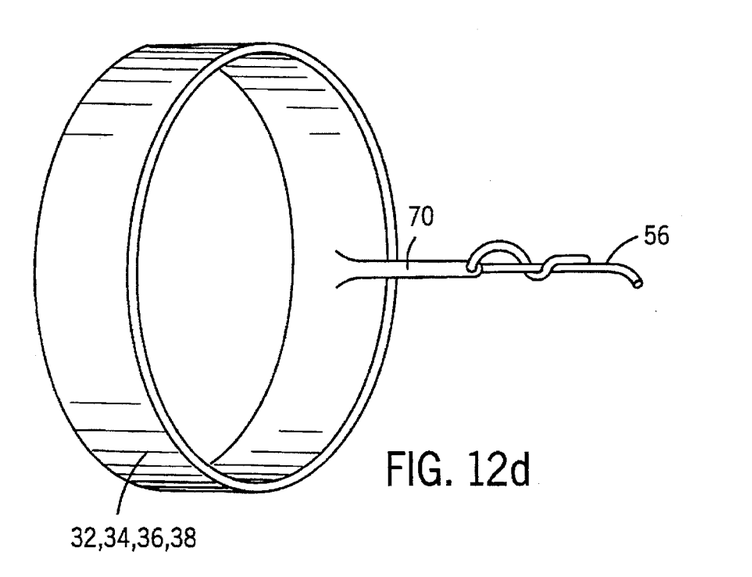

FIGS. 12c and 12d illustrate yet other forms of connection of a lead 56 to one of the electrodes 32, 34, 36, 38. In FIG. 12c, a strap 70 (which may have a flat, round or other cross-sectional shape) of electrically-conductive polymer has been extruded from the surface in the course of making the electrode 32, 34, 36, 38 and connected to a lead 56 with a connector 72 whose ends are crimped onto the strap 70 and the lead 56 respectively. In FIG. 12d, the lead 56 pierces the strap 70 and loops back on itself, where it is secured by knotting, wrapping, adhesive and/or soldering.

In another aspect, the mound 64 is not used and the end 66 of the lead 56 is attached to the inner surface of an electrode with adhesive.

The leads 56 must be guided into handle 20, where they are collected in a connector or outlet 74. By means of a cable 76 extending from the connector or outlet 74, the leads 56 may be connected to an electrical device 78 which may, for example, be a pulse generator, if the device is used in electrotherapy, or an amplifier/display device if it is used in electromyographic biofeedback. Guiding the leads 56 toward the handle 20 may be done in several different ways.

Figure 13:
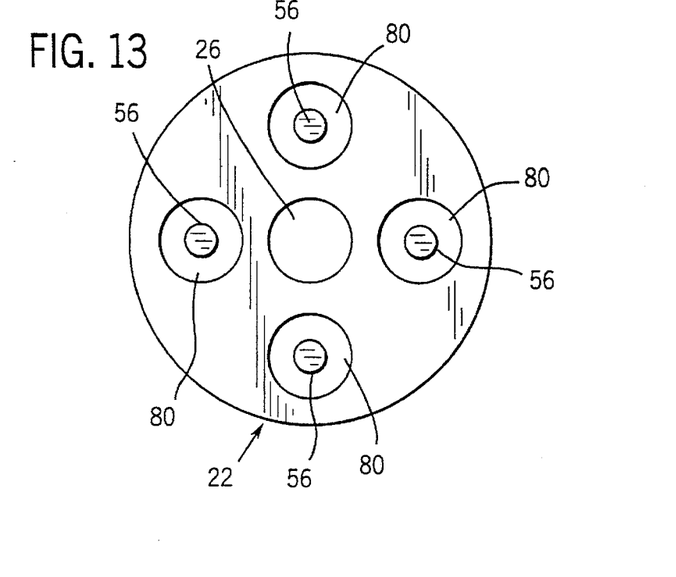
FIGS. 13 and 14 are end views of the rigid cores of the embodiments of FIGS. 2 and 3, respectively.
Figure 14:
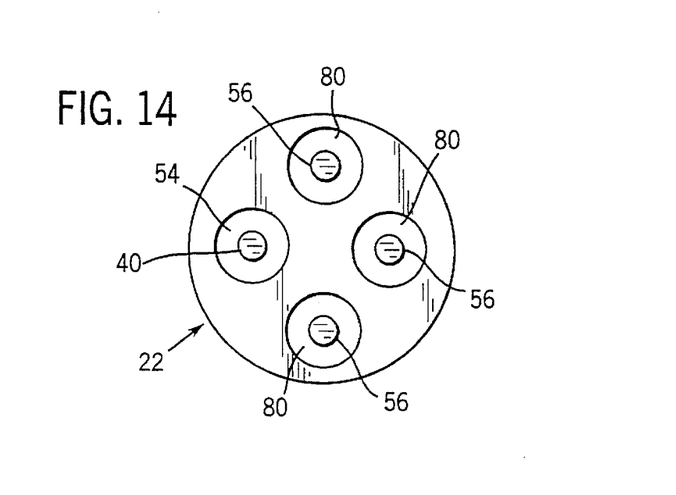

As illustrated in FIGS. 2 and 3, the leads 56 may be directed to one or more passageways 80 formed in the core 22. Examples of such passageways 80 are shown in the end views of the core 22 in FIGS. 13 and 14. The passageways 80 guide leads 56 into the handle 20. Alternatively, as shown in FIG. 4, the leads 56 may be directed toward the handle 20 through the resilient filler member 12 without passing into any passageway in the core 22. In this case, core 22 could be solid and reduced in diameter as shown in FIG. 4 or could be hollowed enough to accommodate an air passageway 26. case of the embodiment of FIGS. 1–4, the lead 56 may be drawn through the mass comprising the resilient filler member 12 by attaching it to a needle which is pushed into and pulled out of the resilient filler member 12.

Figure 15:
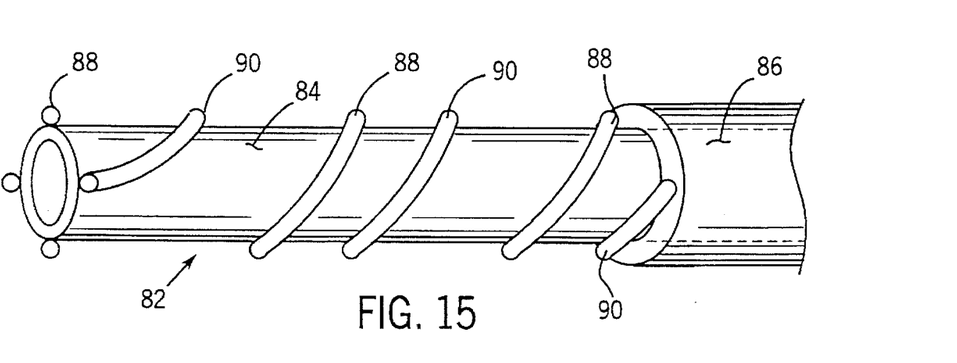
FIGS. 15 illustrates an embodiment of the handle/core in which leads are wound around an inner tube and covered by an outer tube.

FIG. 15 illustrates another embodiment of a structure for guiding the leads 56 from the electrode bands to the exterior of the sheath 14 for connection to the electrical device 78. In that embodiment, the core 82 comprises an inner hollow tube 84 and a co-axial outer tube 86. One or more conductors are wound around the inner tube 84 in a multiple helix fashion. For simplicity, FIG. 15 shows two conductors 88, 90 wound in that fashion, although more could be accommodated. The winding is done so that the two conductors 88, 90 are kept electrically isolated from each other. After that winding has been accomplished, the outer tube 86 is formed over the inner tube 84 and the winding. This may be done in such a way that the material of the outer tube fills in the gaps between the conductors 88, 90 and therefore keeps them electrically isolated. The outer tube 86 may be formed and applied by casting, molding, dipping, co-extruding, crosshead extruding or other methods. To expose the conductors 88, 90 within the sheath 14 for connection to the electrode bands, the intra-sheath portion of the outer tube 86 and be stripped back or the conductors 88, 90 can be pulled to tear them through the intra-sheath portion of the outer tube 86.

The core 22 may be inserted into a receptacle 91 whose inner dimension has approximately the same shape as the core 22 and is slightly larger to allow a snug fit. The core 22 may be secured in the receptacle 91 by friction, an adhesive or another method of adhesion. The receptacle would be formed on or secured to the sheath (in the embodiments illustrated in FIGS. 2–6) or the frame 50 (in the embodiment illustrated in FIGS. 7–10). The receptacle 91 facilitates insertion, helps maintain the insert's shape while in place and reduces the chance that the sheath will disconnect from the core 22 during removal.

FIG. 17 schematically illustrates the electrical circuits formed with electrodes 32, 34, 36, 38 when the device is used in electrotherapy. In one embodiment, the electrical device 78 is a pulse generator 92 having two channels for producing patterns of electrical pulses. The output connections of one channel are electrically connected respectively to electrodes 32 and 38, which are positioned primarily to treat stress incontinency. The contact of electrodes 32 and 38 with selected portions of the vaginal wall 94 completes the circuit between electrodes 32, 38 and one channel of the electrical source. The second channel of the pulse generator 92 is similarly connected to vaginal wall 94 via electrodes 34 and 36 which are positioned primarily to treat urge incontinency.

In electrotherapy, the electrical device 78 is typically a pulse generator 92 capable of forming a train of electrical pulses having characteristics which have been or will be found to be beneficial in the treatment of female urinary incontinence. Various parameters of the electrical signals may be controlled in order to customize a treatment regime for a particular patient. Examples of pulse generators are found in these U.S. Pat. Nos.: 4,515,167, Hochman, May 7, 1985; 4,785,828, Maurer, Nov. 22, 1988; and 4,881,526, Johnson and Maurer, Nov.21, 1989.

In electromyography feedback usages, the electrical device 78 typically amplifies the electrical signals received from the body cavity wall and transforms them into an auditory, tactile or visual display for immediate reception by the patient. See, for example, U.S. Pat. No. 4,396,019, Perry, Jr., Aug. 2, 1983. The insert may include a ground or reference electrode.

As used herein, the term "electrical device" includes devices which transmit electrical energy and devices which receive and process electrical energy, such as by measuring or displaying its characteristics. The invention may transmit electrical energy from the electrical device 78 to the body cavity wall or vice versa.

The outlet 28 of air passageway 24 in the handle 20 may, as shown in FIG. 1, be connected to a pump 96 or other device capable of withdrawing air from the interior of insert 10 and thereby inducing a partial vacuum in it. When the insert 10 is to be inserted into the vagina, pump 96 is used to create a partial vacuum, which causes the resilient filler member 12 to shrink so that the insert 10 is reduced in diameter as shown in FIG. 16. Pump 96 is then removed from outlet 28 and is replaced by plug 30, thereby maintaining the partial vacuum within the insert 10. When the insert 10 has been placed into the desired position in the vagina, plug 30 is removed from outlet 28, which releases the partial vacuum, thereby permitting the resilient filler member 12, the internal ribs, or the separate internal frame to expand the sheath 14 until it engages the vaginal wall. The quantity and material of the resilient filler member 12, and the dimensions and material of the internal ribs or internal frame, are selected so that, within a broad range of vagina sizes, it will exert sufficient force on the vaginal wall to provide efficient electrical conduction and good positional stability. The sheath 14 is elastic to the extent needed to allow it to expand and contract within the same broad range of vaginal sizes. As a result, the electrodes, 32, 34, 36, 38 forcefully, but yieldingly, engage the selected portions of the vaginal wall. For removal of the insert 10, pump 96 may be reattached to outlet 28 and used to shrink insert 10 in the same manner as was done to facilitate easy insertion.

The sheath 14 may be made of biocompatible elastomeric polymers such as silicone rubber, polyurethane, olefinic or styrenic or any of their co-polymers. The electrically-conductive portions of the sheath 14 (electrodes 32, 34, 36, 38) may be made of similar material, but loaded with powdered carbon or a metal, such as copper, silver or gold. The electrodes can be molded as part of the sheath 14 during its manufacture. Alternatively, the electrodes can be glued to the outer surface of the sheath 14, which may in that case be made with reduced-thickness portions onto which the electrodes are then glued. The lead 56 is then pushed through to reduced-thickness portion in order to connect with the electrode. In addition to being elastic for the purpose described above, the sheath 14 should be thin and flexible in order to minimize wrinkles when the insert 10 is in its expanded position.

The resilient filler member 12 within the sheath 14 may be made of an open cell polymer foam, such as polyurethane, silicone rubber or vinyl, or another material having air cells of sufficient number, volume and interconnectedness to allow it to substantially shrink when in a partial vacuum and to substantially expand when the partial vacuum is released. This is the meaning of the term "sponge-like resiliency characteristics" in the claims. The material should be shaped, sized and selected in conjunction with the material and size of sheath 14 so that the resilient filler member 12 is capable of expanding the sheath 14 through a range sufficient to ensure for most vaginal sizes that the sheath 14 is forcefully, but yieldingly, engaged against the vaginal wall.

The core 22 may be made of a silicone or polycarbonate material and preferably is semi-rigid. The end of core 22 which is adjacent the end of insert 10 which is first inserted into the vagina may be rounded and/or slightly enlarged to reduce the risk of tearing the sheath 14. The end of the sheath 14 may be reinforced for the same reason.

The collar 16 of the sheath 14 may be affixed to the neck 18 of the handle 20 by hermetic, adhesive, clamp or other means. The junction between collar 16 and neck 18 should be substantially airtight.

To use the device for electrical stimulation of muscles, the patient or care giver connects the insert's leads 56 to a source of electrical signals; connects the pump 96 to the insert aperture; operates the pump 96 to evacuate the air from the insert 10; closes the aperture with the plug; places the insert 10 in the body cavity; and turns on the electrical signals to stimulate the target muscles. After the therapy session, the patient or caregiver turns off the electrical signals; removes the plug and attaches the pump 96; operates the pump 96 to shrink the insert 10; and removes the insert 10.

For electromyographical biofeedback treatments, the procedure for insertion and removal is approximately the same. The electrical device 78 is not the source of electrical signals, but rather receives, processes and creates a display of the electrical impulses generated by the patient's exercising of muscles near the body cavity.

Although the preferred embodiments of the invention have been described above, the invention claimed is not so restricted. There may be various other modifications and changes to these embodiments which are within the scope of the invention.

We claim:

1. A method of monitoring electrical energy generated by exercising muscles near a body cavity by transmitting such energy from a wall of the body cavity to an electrical processor, comprising the steps of:

(a) providing a substantially airtight sheath having a resilient skeleton which in the absence of opposing forces provides the sheath with a shape and size such that the sheath yieldingly impinges on the body cavity wall when the sheath is installed in the body cavity, the sheath having at least a pair of electrically conductive portions insulated from each other and an airflow aperture in the sheath;

(b) providing a pump and placing it removably in communication through the aperture with air in the sheath such that operating the pump evacuates air from the sheath and thereby collapses the sheath;

(c) collapsing the sheath by operating the pump;

(d) removing the pump and closing the aperture;

(e) inserting the sheath in the body cavity;

(f) opening the aperture to allow air to return into the sheath so that the resilient skeleton expands and the conductive portions yieldingly and conductively engage the body cavity wall;

(g) electrically connecting the conductive portions to the electrical processor;

(h) exercising muscles near the body cavity so that muscle-activity electrical energy flows from the body cavity wall through one conductive portion to the electrical processor and thence into the other conductive portion and back to the body cavity wall;

(i) electrically disconnecting the electrical processor from the conductive portions; and (j) placing the pump in communication with the aperture, operating the pump to collapse the sheath and removing the insert.

2. A body cavity insert for transmitting electrical energy between a body cavity wall and an electrical device, comprising:

(a) a substantially airtight, flexible sheath which comprises at least a pair of flexible, electrically conductive portions insulated from each other and an airflow port;

(b) a resilient skeleton located within the sheath and adapted to form and hold the sheath yieldingly against the body cavity wall when the insert is installed in the body cavity;

(c) a plurality of electrical leads connected one to each electrically conductive portion and disposed for connection to the electrical device;

(d) a pump adapted for attachment to the port such that operation of the pump evacuates air from the sheath and thereby collapses the sheath and the skeleton to facilitate insertion of the body cavity insert into and its removal from the body cavity;

(e) a substantially airtight barrier adapted to be positioned to close the port to prevent inflow of air and thereby maintain the sheath in a collapsed state during insertion and removal and to be positioned to open the port to enable air to return to the sheath so that the resilient skeleton expands the sheath; and (f) wherein the resilient skeleton comprises a frame made of a plurality of resilient frame members, the frame being substantially separate from the sheath.

3. A body cavity insert as in claim 2, wherein at least one of the resilient frame members is located so as to substantially underlie at least one of the electrically conductive portions.

4. A body cavity insert for transmitting electrical energy between a body cavity wall and an electrical device, comprising:

(a) a substantially airtight, flexible sheath which comprises at least a pair of flexible, electrically conductive portions insulated from each other and an airflow port;

(b) a resilient skeleton located within the sheath and adapted to form and hold the sheath yieldingly against the body cavity wall when the insert is installed in the body cavity;

(c) a plurality of electrical leads connected one to each electrically conductive portion and disposed for connection to the electrical device;

(d) a pump adapted for attachment to the port such that operation of the pump evacuates air from the sheath and thereby collapses the sheath and the skeleton to facilitate insertion of the body cavity insert into and its removal from the body cavity;

(e) a substantially airtight barrier adapted to be positioned to close the port to prevent inflow of air and thereby maintain the sheath in a collapsed state during insertion and removal and to be positioned to open the port to enable air to return to the sheath so that the resilient skeleton expands the sheath; and (f) an elongated, substantially rigid core in the sheath, wherein the core comprises an inner tube, an outer tube located coaxially with the inner tube and a plurality of electrical conductors wound helically around the inner tube, wherein the electrical conductors are electrically insulated from each other between the inner tube and the outer tube and are adapted for electrically connecting the electrical lead with the electrical device.

5. A body cavity insert as in claim 4, wherein the electrical insulation is provided by inward extensions of an inner surface of the outer tube.

6. A body cavity insert as in claim 4, wherein the core is hollow, perforated and in fluid communication with the port.

7. A body cavity insert for transmitting electrical energy between a body cavity wall and an electrical device, comprising:

(a) a substantially airtight, flexible sheath which comprises at least a pair of flexible, electrically conductive portions insulated from each other and an airflow port;

(b) a resilient skeleton located within the sheath and adapted to form and hold the sheath yieldingly against the body cavity wall when the insert is installed in the body cavity;

(c) a plurality of electrical leads connected one to each electrically conductive portion and disposed for connection to the electrical device;

(d) a pump adapted for attachment to the port such that operation of the pump evacuates air from the sheath and thereby collapses the sheath and the skeleton to facilitate insertion of the body cavity insert into and its removal from the body cavity;

(e) a substantially airtight barrier adapted to be positioned to close the port to prevent inflow of air and thereby maintain the sheath in a collapsed state during insertion and removal and to be positioned to open the port to enable air to return to the sheath so that the resilient skeleton expands the sheath;

(f) an elongated, substantially rigid core in the sheath; and (g) a receptacle secured to an inner wall of the sheath and disposed to receive an end of the core.

8. A body cavity insert for transmitting electrical energy between a body cavity wall and an electrical device, comprising:

(a) a substantially airtight, flexible sheath which comprises at least a pair of flexible, electrically conductive portions insulated from each other and an airflow port;

(b) a resilient skeleton located within the sheath and adapted to form and hold the sheath yieldingly against the body cavity wall when the insert is installed in the body cavity;

(c) a plurality of electrical leads connected one to each electrically conductive portion and disposed for connection to the electrical device;

(d) a pump adapted for attachment to the port such that operation of the pump evacuates air from the sheath and thereby collapses the sheath and the skeleton to facilitate insertion of the body cavity insert into and its removal from the body cavity;

(e) a substantially airtight barrier adapted to be positioned to close the port to prevent inflow of air and thereby maintain the sheath in a collapsed state during insertion and removal and to be positioned to open the port to enable air to return to the sheath so that the resilient skeleton expands the sheath: and (f) wherein a portion of each of the leads is conductively embedded in one of the conductive portions and wherein the embedded portion extends along at least a substantial portion of the conductive portion around the sheath.

9. A body cavity insert for transmitting electrical energy between a body cavity wall and an electrical device, comprising:

(a) a substantially airtight, flexible sheath which comprises at least a pair of flexible, electrically conductive portions insulated from each other and an airflow port;

(b) a resilient skeleton located within the sheath and adapted to form and hold the sheath yieldingly against the body cavity wall when the insert is installed in the body cavity;

(c) a plurality of electrical leads connected one to each electrically conductive portion and disposed for connection to the electrical device;

(d) a pump adapted for attachment to the port such that operation of the pump evacuates air from the sheath and thereby collapses the sheath and the skeleton to facilitate insertion of the body cavity insert into and its removal from the body cavity;

(e) a substantially airtight barrier adapted to be positioned to close the port to prevent inflow of air and thereby maintain the sheath in a collapsed state during insertion and removal and to be positioned to open the port to enable air to return to the sheath so that the resilient skeleton expands the sheath; and (f) wherein a portion of each of the leads is conductively embedded in one of the conductive portions and wherein the conductive portion comprises two layers and the embedded portion of the lead is sandwiched between them.

10. A body cavity insert for transmitting electrical energy between a body cavity wall and an electrical device, comprising:

(a) a substantially airtight, flexible sheath which comprises at least a pair of flexible, electrically conductive portions insulated from each other and an airflow port;

(b) a resilient skeleton located within the sheath and adapted to form and hold the sheath yieldingly against the body cavity wall when the insert is installed in the body cavity;

(c) a plurality of electrical leads connected one to each electrically conductive portion and disposed for connection to the electrical device;

(d) a pump adapted for attachment to the port such that operation of the pump evacuates air from the sheath and thereby collapses the sheath and the skeleton to facilitate insertion of the body cavity insert into and its removal from the body cavity;

(e) a substantially airtight barrier adapted to be positioned to close the port to prevent inflow of air and thereby maintain the sheath in a collapsed state during insertion and removal and to be positioned to open the port to enable air to return to the sheath so that the resilient skeleton expands the sheath: and (f) a conductive mound formed on at least one of the conductive portions and wherein at least one of the electrical leads pierces said mound thereby forming a junction and further comprising adhesive spread on and around the junction of the conductive mounds and said at least one of the electrical leads.

11. A body cavity insert for transmitting electrical energy between a body cavity wall and an electrical device, comprising:
 (a) a substantially airtight, flexible sheath which comprises at least a pair of flexible, electrically conductive portions insulated from each other and an airflow port;
 (b) a resilient skeleton located within the sheath and adapted to form and hold the sheath yieldingly against the body cavity wall when the insert is installed in the body cavity;
 (c) a plurality of electrical leads connected one to each electrically conductive portion and disposed for connection to the electrical device;
 (d) a pump adapted for attachment to the port such that operation of the pump evacuates air from the sheath and thereby collapses the sheath and the skeleton to facilitate insertion of the body cavity insert into and its removal from the body cavity;
 (e) a substantially airtight barrier adapted to be positioned to close the port to prevent inflow of air and thereby maintain the sheath in a collapsed state during insertion and removal and to be positioned to open the port to enable air to return to the sheath so that the resilient skeleton expands the sheath; and
 (f) a conductive mound formed on at least one of the conductive portions and wherein at least one of the electrical leads pierces said mound thereby forming a junction and wherein an end of said at least one of the electrical leads through-pierces the conductive mound and is connected to a portion of said at least one of the electrical leads near the junction.

12. A body cavity insert for transmitting electrical energy between a body cavity wall and an electrical device, comprising:
 (a) a substantially airtight, flexible sheath which comprises at least a pair of flexible, electrically conductive portions insulated from each other and a port;
 (b) a resilient skeleton located within the sheath and adapted to form and hold the sheath yieldingly against the body cavity wall when the insert is installed in the body cavity;
 (c) a plurality of electrical leads connected one to each electrically conductive portion and disposed for connection to the electrical device;
 (d) a pump adapted for attachment to the port such that operation of the pump evacuates air from the sheath and thereby collapses the sheath and the skeleton to facilitate insertion of the body cavity insert into and its removal from the body cavity;
 (e) a substantially airtight barrier adapted to be positioned to close the port to prevent inflow of air and thereby maintain the sheath in a collapsed state during insertion and removal and to be positioned to open the port to enable air to return to the sheath so that the resilient skeleton expands the sheath; and
 (f) an elongated, electrically-conductive strap formed on at least one of the conductive portions.

13. A body cavity insert as in claim 12, in which at least one of the electrical leads is connected to said strap by crimping.

14. A body cavity insert as in claim 12, in which an end of said at least one of the electrical leads through-pierces the strap at a junction and is connected to a portion of said at least one of the electrical leads near the junction.

\* \* \* \* \*